Figure 1:
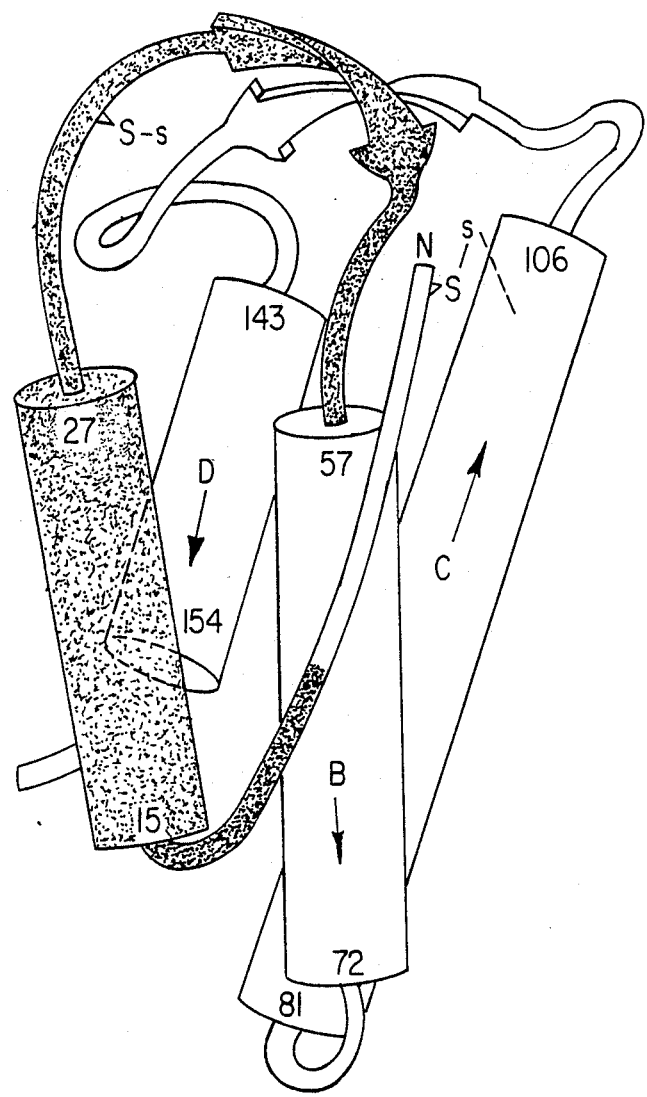

United States Patent [19]

Bell et al.

[11] Patent Number: 4,914,033

[45] Date of Patent: Apr. 3, 1990

[54] STRUCTURE AND PROPERTIES OF MODIFIED INTERFERONS

[75] Inventors: Leslie D. Bell, Thame; Paul G. Boseley; Alan G. Porter, both of High Wycombe, all of England

[73] Assignee: G. D. Searle & Co., Chicago, Ill.

[21] Appl. No.: 195,232

[22] Filed: May 18, 1988

Related U.S. Application Data

[62] Division of Ser. No. 730,017, May 3, 1985, Pat. No. 4,769,233.

[30] Foreign Application Priority Data

May 17, 1984 [GB] United Kingdom ............... 8412564

[51] Int. Cl.⁴ .................. C12N 1/20; C12N 15/00; C07H 21/04
[52] U.S. Cl. .................. 435/252.3; 434/252.33; 434/320; 536/27
[58] Field of Search ................ 435/252.3, 252.33, 320, 435/68; 536/27

[56] References Cited

U.S. PATENT DOCUMENTS 4,569,908 2/1986 Mark et al. ........................ 435/68

4,588,585 5/1986 Mark et al. ........................ 435/68

OTHER PUBLICATIONS

Goeddel, D. et al., Nucleic Acids Research, vol. 8, No. 18, pp. 4057–4074, 1980.
Shepard, H. et al., Nature, vol. 294, pp. 563–565, 1981.

*Primary Examiner*—Blondel Hazel
*Attorney, Agent, or Firm*—Mary Jo Kanady; Paul D. Matukaitis

[57] ABSTRACT

A composition of matter comprising a polypeptide of the formula:

$$A-R_1-B-R_{2-22}-C$$

wherein
A is the amino acid sequence 1–16 of human beta interferon;
$R_1$ is cysteine, serine or alanine;
B is the amino acid sequence 18–31 of human beta interferon;
$R_{2-22}$ are naturally occurring amino acids;
C is the amino acid sequence 53–166 of human beta interferon.

12 Claims, 4 Drawing Sheets

FIG. 2a

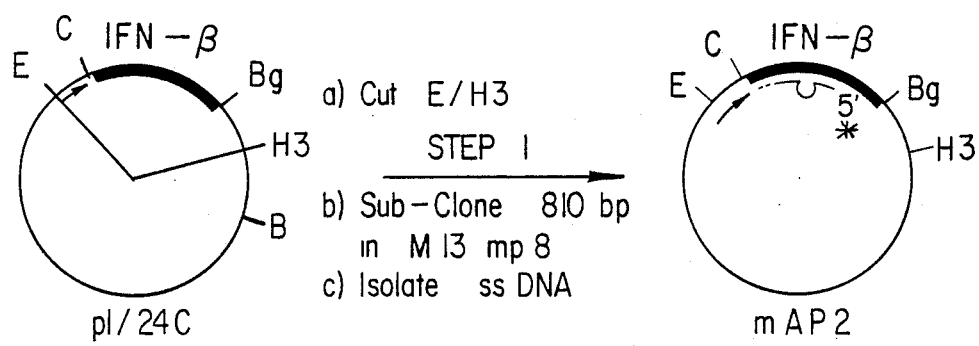

a) Cut E/H3
   STEP 1
b) Sub-Clone 810 bp in M13 mp 8
c) Isolate ss DNA a) Anneal Mismatch primer *
   * 5'-CAGTGCTCGAGGAATCTTGTC-3',
   pol. I fill, ligate, transform
   E. Coli JM 101 b) Grow in shake flask, isolate plasmid DNA, check partially cut with Xho I (C↓TCGAG)

STEP 2

Mixture of:—

|  | 74 | 75 | 76 ← CODON |
|---|---|---|---|
| Mutant Sequence | TCC | TCG | AGC |
| Wild Type Sequence | TCA | TCT | AGC |
|  | —Ser— | Ser— | Ser— |

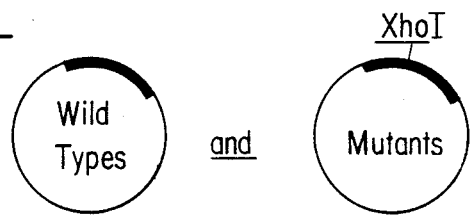

Wild Types and Mutants a) Cut (partially) Xho I, isolate linear DNA.
b) Religate, transform E. coli JM 101, check all clones cut with Xho I

STEP 3 mAP3

EXPRESSION OF IFNX416 AND IFN-$\beta$ PROTEIN AT 1 AND 4 HOURS AFTER INDUCTION OF THE TRP PROMOTER. THE POSITION OF THE IFN BAND IS INDICATED BY AN ARROW.
20K REFERS TO A 20,000 DALTONS MARKER.

STRUCTURE AND PROPERTIES OF MODIFIED INTERFERONS

This is a division of application Ser. No. 06/730,017, filed May 3, 1985, now U.S. Pat. No. 4,769,233.

BACKGROUND OF THE INVENTION

1. Field of the Invention

This invention describes the use of recombinant DNA technology for the design and synthesis of novel modified interferons. More specifically the invention relates to interferons not known in nature, which are intended for use in viral and neoplastic diseases, and immunosuppressed and immunodeficient conditions, as they exhibit new and unexpected biological properties.

2. Description of the Prior Art

The interferons are a class of proteins that occur in vertebrates and act as biological regulators of cell function which include increasing resistance to pathogens, limiting cell growth and modulating the immune system. The most studied property of the interferons is their ability to convert cells into an "antiviral state" during which they are more resistant to virus replication (Lengyel, Annual Review of Biochemistry, 51, 251, 1982). In addition to conferring antiviral resistance to target cells, interferons (IFNs) have antiproliferative (antigrowth) properties (Stewart, 1979, The Interferon System, Springer, Berlin). It has clearly been shown that interferons produced naturally act as antiviral and antiproliferative agents (Gresser et al., Biochim. Biophys. Acta, 516, 231, 1978; J. Exp. Med., 144, 1316, 1976).

The IFNs, by virtue of their antigenic, biological and physico-chemical properties, may be divided into three classes: type I, IFN-α ("leucocyte") and IFN-β ("fibroblast"); and type II, IFN-γ. Human IFN-α is specified by a multigene family comprising at least 20 genes. The classification of IFNα and IFN-β as type I interferons is in part determined by their significant degree of homology, 23% at the protein level (Taniguchi et al., Nature, 285, 547, 1980).

While the mechanism of action of interferons is not completely understood, certain physiological or enzymatic activities respond to the presence of the interferons. These activities include RNA and protein synthesis. Among the enzymes induced by interferons is (2'-5'). (A)n synthetase which is activated by double-stranded RNA. This synthetase generates 2'-5' linked oligonucleotides, and these in turn activate a latent endoribonuclease, RNAse L, which cleaves single-stranded RNA, such as messenger RNA (mRNA) and ribosomal RNA (rRNA). Also induced by IFNs is a protein kinase that phosphorylates at least one peptide chain initiation factor and this inhibits protein synthesis (Lengyel, ibid, p.253). IFNs have been shown to be negative growth regulators for cells by regulation of the (2'-5')An synthetase activity (Creasey et al., Mol. and Cell Biol., 3, 780, 1983). IFN-β was indirectly shown to be involved in the normal regulation of the cell cycle in the absence of inducers through the use of anti-IFN-β antibodies. Similarly, IFNs have been shown to have a role in differentiation (Dolei et al., J. Gen. Virol., 46, 227, 1980) and in immunomodulation (Gresser, Cell. Immunol., 34, 406, 1977). Finally, IFNs may alter the methylation pattern of mRNAs and alter the proportion of fatty acids in membrane phospholipids, thereby changing the rigidity of cell membranes.

These and other mechanisms may respond to interferon-like molecules in varying degrees depending on the structure of the interferon-like polypeptide. Preliminary evidence (U.K. Patent GB 2,090,258A) suggests that members of the multigene IFN-α family vary in the extent and specificity of their antiviral activity (Pestka, ibid.) For example, combination of IFN-αA with IFN-αD resulted in "hybrid" genes which show antiviral properties that are distinct from either parent molecule (Weck et al., Nucl. Acids Res., 9, 6153, 1981). However, hybrid human IFNs with substantially increased human cell activity/specificity have not yet been developed. One Patent Application has been published describing IFN-β/α hybrids (PCT/US83/0077). This patent is an initial attempt to form modified IFNs, however, they do not disclose the substantially modified structures or activity of the present invention.

ADDITIONAL RELEVANT PATENT APPLICATIONS

U.K. No. GB 2,116,566A—Animal interferons and processes for their production.

U.S. Pat. No. 4,414,150—Hybrid human leukocyte interferons. U.K. No. GB 2,068,970A—Recombinant DNA technique for the preparation of a protein resembling human interferon.

SUMMARY OF THE INVENTION

1. A composition of matter comprising a polypeptide of the formula:

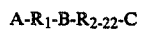

$$A\text{-}R_1\text{-}B\text{-}R_{2\text{-}22}\text{-}C$$

wherein:
A is the amino acid sequence 1–16 of human beta interferon;
$R_1$ is cysteine, serine or alanine;
B is the amino acid sequence 18–31 of human beta interferon;

$R_{2\text{-}22}$ are naturally occurring amino acids;

C is the amino acid sequence 53–166 of human beta interferon.

The superior properties of the modified beta interferons described in this invention indicate the critical importance of the amino acids sequentially numbered 32 to 52 from the amino terminus of the beta interferon polypeptide. It is anticipated that additional amino acid substitutions in this area will result in polypeptides having similar superior properties. The substitution of one to twenty-one amino acids into the beta interferon between these amino acids can be any of the twenty naturally occurring amino acids with any one amino acid optionally repeated. A preferred embodiment of this invention replaces the beta interferon amino acids numbered 36 to 48 from the amino terminus. Another preferred embodiment of this invention replaces five to thirteen of the amino acids in beta interferon between 36 to 48 with a sequence from the alpha interferon amino acids numbered 34 to 46. One example of the preferred alpha interferon replacement is the amino acids from the alpha 1 interferon amino acids 34 to 46. All amino acid numbering is sequential from the amino to the carboxy terminus. Yet another example of a modified beta interferon is the replacement of beta interferon amino acids 36 to 40 by the alpha 1 amino acids 34 to 38. Still another modified beta interferon has the beta amino acids 42 to 48 replaced by the alpha 1 amino acids 40 to 46. The modified interferons described may be of human or other mammalian origin. The cysteine 17 of the beta interferon may optionally be replaced by serine 17 or alanine 17 in all of the modified beta interferons.

The sequence of interferon beta amino acids replaced by the amino acids of an alpha interferon are sequential. Sequential means amino acids in sequence from the amino terminus to the carboxy terminus in either a contiguous or non-contiguous sequence.

The novel, modified beta interferons may have one or more of the antiviral, cell growth regulating or immunomodulatory activities substantially changed from that of the unmodified beta interferon. Among these embodiments of this invention are IFNX416, IFNX417 and IFNX418, IFNX430, IFNX444, IFNX445, IFNX446, IFNX447, IFNX448, IFNX449, IFNX456 and IFNX485. A recombinant beta interferon antiviral, cell growth regulating or immunomodulatory activity is considered to be substantially changed when one or more activities are increased or decreased greater than about 2-fold.

Another embodiment of the invention is a DNA or RNA sequence coding for the synthesis of the modified beta interferons. Still another embodiment is recombinant plasmids containing the DNA sequences coding for the modified beta interferons. Yet another embodiment is a cell transformed by a recombinant plasmid of this invention which produces a modified beta interferon. Also disclosed is a process for producing the modified beta interferon in transformed cells, either prokaryotic or eukaryotic.

An object of the invention is to produce modified interferons that display a new advantageous phenotype. These new interferon-like polypeptides composed of portions of IFN-$\beta$ and other amino acid sequences are advantageous for one or more of the following reasons:

1. The new IFNs show a greater, e.g. antiproliferative to antiviral activity (and vice versa) resulting from the selective activation of only some of the normal interferon-induced biochemical pathways.

2. The affinity of hybrid or modified IFNs for cell surface receptors differ from that of naturally occurring interferons. This allows selective or differential targeting of interferons to a particular cell type, or increased affinity for the receptor—leading to increased potency against a particular virus disease or malignancy.

3. The novel IFNs have an increased therapeutic index, excluding some of the undesirable side effects of natural IFNs which limit their use (Powledge, TM, Biotechnology, 2, 214, March 1984).

4. The novel IFNs include in the design structures which allow increased stability to proteolytic breakdown during microbial synthesis.

5. The novel IFNs increase their solubility or stability in vivo, and prevent non-specific hydrophobic interactions with cells and tissues.

6. The novel IFNs are more readily recovered from the microbial supernatant or extract, and more easily purified.

A pharmaceutical composition containing a modified beta interferon is described in combination with a pharmaceutically acceptable carrier. This pharmaceutical composition may be administered in an effective amount by oral, parenteral, or other routes which result in antiviral, cell growth regulating or immunomodulatory activities.

In one embodiment of the invention, recombinant DNA technologies were successfully applied to produce synthetic DNA sequences, which in combination with natural and synthetic IFN-$\beta$ gene sequences, direct the efficient expression of new polypeptides, each having an IFN-like structure. These novel, IFN-like molecules, examples of which are given in the present invention, display new and unexpected biological properties.

One embodiment of the present invention is the creation of novel IFNs displaying substantially increased antiviral and/or antiproliferative and/or immunostimulating activities compared with IFN-$\beta$ produced by *E. coli*. These increased antiviral, antiproliferative and immunostimulating activities were unexpected since similar amino acid changes as described in this disclosure were found previously in other modified interferons to result in *reduced* antiviral and immunostimulating activities, and unchanged antiproliferative activity when compared to recombinant IFN-$\beta$.

BRIEF DESCRIPTION OF THE DRAWINGS AND CHARTS AND TABLES

FIG. 1 A predicted structure of IFN-$\beta$ and IFN-$\alpha_1$ (Sternberg and Cohen, Int. J. Biol. Macromol., 4, 137, 1982). The amino acids 36–48 of IFN-$\beta$ lie in a predicted "loop" region between the A and B $\alpha$-helical "bundles".

FIGS. 2*a, b* Illustrate the path to construction of the plasmid vector expressing IFNX416.

FIG. 3 Shows the expression level of IFNX416 compared to IFN-$\beta$ in *E. coli* (polyacrylamide gel).

Charts 1a–c Show the ligated oligonucleotides used in the construction of IFNX416, IFNX417 and IFNX418.

Charts 2a–1 Show the complete amino acid sequence and nucleotide sequences of the genes coding for IFNX416, IFNX417 and IFNX418, IFNX430, IFNX444, IFNX445, IFNX446, IFNX447, IFNX448, IFNX449, IFNX456 and IFNX485.

Chart 3 Shows the nucleotide sequence of the trp promoter used to initiate transcription of the genes.

Table 1 Compares expression, antiviral activities and antiproliferative activities in bacterial extracts for IFN-$\beta$, IFNX416, IFNX417 and IFNX418.

Table 2 Compares antiviral activity of purified IFN-$\beta$, IFN-$\beta$:$Ser^{17}$, IFNX416 and IFNX418 on some cell lines.

Table 3 Compares antiproliferative activities on some cell lines of purified IFN-$\beta$, IFN-$\beta$:$Ser^{17}$, IFNX416 and IFNX418.

Table 4 Compares stimulation of Antibody Dependent Cellular Cytotoxicity (ADCC) by purified IFN-$\beta$, IFN-$\beta$:$Ser^{17}$, IFNX416 and IFNX418.

Table 5 Summary of the Oligonucleotides used in site-directed mutagenesis during construction of IFNX-444-49 and method for construction of IFNX456 and 485.

DETAILED DESCRIPTION OF THE PREFERRED EMBODIMENTS

Previously, IFN-$\beta$ exhibited a low specific antiviral activity when produced in *E. coli*, about $3\text{–}5 \times 10^6$ units/mg protein, which is $\sim 1\%$ of the activity of natural, glycosylated IFN-$\beta$ from fibroblast cells. Recently, a similar low specific activity for recombinant IFN-$\beta$ was reported by Petteway et al., Fourth Int. Congress for Recombinant DNA, San Diego, CA—February 19–22, 1984. This low specific activity may be due to instability, denaturation and/or incorrect folding of the unglycosylated molecule during biosynthesis in *E. coli*.

In an attempt to overcome this problem, one publication claimed that the change of amino acid residue 17 from cysteine to serine increased the specific antiviral activity of recombinant IFN-β. (Patent Application GB 2,130,219). Accordingly in some examples, the cysteine 17 to serine 17 change is incorporated in combination with the modified beta interferons of this invention.

The novel IFNs in the present disclosure either possess inherently increased antiviral and/or antiproliferative and/or immunostimulating activities, or refold during renaturation to a structure exhibiting the high specific activity of natural, glycosylated IFN-β, or some combination of both. The class of novel, modified IFNs, examples of which are disclosed in the present invention, are more effective than recombinant IFN-β or other recombinant IFNs in the treatment of viral or neoplastic diseases, or immunodeficient or immunosuppressed conditions since they possess higher biological activity than recombinant IFN-β. Higher biological activity than recombinant IFN-β can result in an improved therapeutic index, which excludes some of the side effects caused by the use in humans of unmodified recombinant or naturally occurring IFNs.

INTRODUCTION

The IFN-β gene is a unique gene but shows some significant homologies to the multigenic IFN-α family (Rubinstein, Biochim. Biophys. Acta, 695, 5, 1982). Sternberg and Cohen (Int. J. Biol. Macromol., 4, 137, 1982) have proposed a similar secondary and tertiary structure for IFN-β and IFN-$α_1$. Structure prediction studies suggest four α-helices which can be "packed" into a right-handed bundle (FIG. 1) similar to that observed in several unrelated protein structures as determined by X-ray crystallography. In part the design of the modified interferons described herein is derived from our interpretation of the Sternberg/Cohen model. Since IFNs α and β are believed to bind to the same receptor at the cell surface it is possible to introduce variability into IFN-β by replacing specific areas with IFN-α segments. Previously the construction of other modified interferons (European patent application Nos. 84,107,458.6, 84,107,498.2, 84,107,456.0, and 84,107,457.8) resulted in novel, hybrid IFNs with altered biological properties in some cases. These interferons were active to some degree, suggesting a large measure of variability in the nature of the inserted amino acid sequence which would give rise to an active molecule.

Accordingly, the field of the present invention is the design, synthesis and characterization of interferon-like molecules related to IFN-β which may have amino acid sequences from the 32–52 region of IFN-β replaced with any other amino acid sequence, unrelated protein sequence, or sequences similar to those of IFN-α's or -β's found in mammals and other vertebrates.

Among the amino acids that may be substituted for any individual β interferon amino acid from position 32 to 52 are the following naturally occurring amino acids: alanine, valine, leucine, isoleucine, proline, phenylalanine, tryptophan, methionine, glycine, serine, threonine, cysteine, tyrosine, asparagine, glutamine, aspartic acid, glutamic acid, lysine, arginine or histidine.

Through binding of hybrid IFN-$\alpha$'s ($\alpha_1$ and $\alpha_2$ in Streuli et al., Proc. Natl. Acad. Sci. U.S.A., 78, 2848, 1981), an attempt was made to analyse the number and nature of idiotypes involved in the receptor binding site of IFN-$\alpha$'s. Two sites were proposed as constituting the binding site, one in the amino-terminal half and the other in the carboxy-terminal half of IFN-$\alpha$. The two major regions of partial homology between IFN-$\alpha$'s and IFN-$\beta$ occur between amino acid residues 28–80 and 115–151 which may well correspond to the above-mentioned idiotypes. Evidence that the 28–80 region may be important in receptor binding come from the finding that polyclonal antibodies raised against a synthetic peptide composed of IFN-$\alpha_2$ amino acids 24–81, bind to IFN-$\alpha_2$ and prevent it interacting with its cell receptor (Dreiding, TNO Interferon Meeting, Rotterdam, 1983). Since IFNX402 (IFN-$\beta$[$\beta$(9–56)]-[$\alpha_1$(-7–54)]) displays dramatically reduced human cell antiviral and immunostimulating activities relative to antiproliferative activity (European patent application 84,107,498.2), examples of novel interferons derived from IFN-$\beta$ having altered amino acids between residues ~28 and ~54 were among those synthesized. The following are examples of modified interferon $\beta$ molecules with altered amino acids between residues 28 and 54.

IFNX416=IFN$\beta$[$\beta$(36–48)]→[$\alpha_1$(34–46]; [$CYS^{17}$]→[$SER^{17}$]

IFNX417=IFN$\beta$[$\beta$(36–40)]→[$\alpha_1$(34–38)];-[$CYS^{17}$]→[$SER^{17}$]

IFNX418=IFN$\beta$[$\beta$(42–48)]→[$\alpha_1$(40–46)]

IFNX430=IFN$\beta$[$\beta$(36–48)]→[$\alpha_1$(34–46)]

IFNX444=IFN$\beta$[$ASP^{39}$]→[$GLY^{39}$]

IFNX445=IFN$\beta$[$leu^{47}$]→[$gly^{47}$]

IFNX446=IFN$\beta$[$asp^{39}$]→[$gly^{39}$];[$leu^{47}$]→[$gly^{47}$]

IFNX447=IFNX416[$gly^{39}$→$Arg^{39}$];[$phe^{40}$→$Ile^{40}$]

IFNX448=IFNX416[$His^{36}$→$lys^{36}$];[$asp^{37}$→$tyr^{37}$]

IFNX449=IFNX416[$gln^{42}$→$gly^{42}$]

IFNX456=IFN$\beta$[$\beta$(36–48)]→[$\alpha_8$(34–46)]

IFNX485=IFN$\beta$[$\beta$(36–48)]→[mouse$\beta$(34–45)];-[$cys^{17}$]→[$ser^{17}$]

IFNX416 contains the amino acid sequence of human IFN-$\beta$ wherein amino acids 36–48 inclusive of the mature IFN-$\beta$ are replaced by the amino acids 34–46 inclusive of mature IFN-$\alpha_1$. Similarly, IFNX417 has the amino acid sequence of IFN-$\beta$ except that amino acids 36–40 are replaced by IFN-$\alpha_1$ amino acids 34–38 inclusive, and so on. Since amino acid 34 of IFN-$\alpha_1$ corresponds to amino acid 36 of IFN-$\beta$, the equivalent regions of both IFNs are exchanged (Taniguchi et al., ibid). Apart from the cysteines at residue 17 being replaced by serine, the rest of the IFNX416 and IFNX417 protein have the same amino acid sequence as IFN-$\beta$. IFNX418 has cysteine at position 17.

Also relevant to the present invention is our finding that certain amino acid changes to IFNX416 between IFN-$\beta$ amino acid residues 32 and 52 potentiate the antiviral and/or antiproliferative response in part by improving renaturation to an active IFN-like structure, increasing solubility and stability, increasing hydrophilicity and decreasing hydrophobicity, or as a result of some combination of the above.

The following examples illustrate the invention and are not intended to limit the scope of the invention in any way. They describe techniques used in the design, chemical synthesis and insertion of DNA fragments in part of the human IFN-β gene. Also described is the expression in *E. coli* and some biological properties of IFNX416, IFNX417 and IFNX418. The techniques described will be familiar to anyone skilled in the art.

EXAMPLE 1. DESIGN AND SYNTHESIS OF GENES AND PLASMIDS

Design of the Synthetic Gene Fragments

The nucleotide sequences of each synthetic ClaI-XhoI DNA fragment (Charts 1a and 1b) were designed utilizing the following criteria:

1. Codon utilization of the $\alpha_1(34-46)$ part of the sequence was optimized for expression in *E. coli*.
2. The codons for the remaining IFN-β sequence between the ClaI and XhoI sites (Charts 1 and 2) were the same as the natural IFN-β gene, except for TGT(Cys$^{17}$)→TCT(Ser$^{17}$); TCA(Ser-74)→TCC; and TCT(Ser-75)→TCG. The latter two changes are "silent" and were merely to preserve the XhoI site (CTCGAG), originally inserted by site-directed mutagenesis (FIG. 2). Natural IFN-β gene sequences were used as far as possible in order to obtain levels of expression of IFNX416, IFNX417 and IFNX418 from plasmids pAP8, pNW31 and pAP9, respectively, as high as that of IFN-β (FIG. 3) from plasmid pGC10 (Chart 5). Plasmid pGC10 is identical to p1/24C (FIG. 3a) except that the ~546bp BglII-BamHI fragment is deleted. Plasmid p1/24C is identical to p1/24 except for the underlined sequence in Chart 4 (see U.K. Pat. No. 8,102,051).
3. Sequences which might anneal to each other in the assembly of the ClaI-XhoI fragments (Chart 1) were removed (within the limits allowed by the redundancy in the genetic code) from codons 36–48 in IFNX416, 36–40 in IFNX417 and 42–48 in IFNX418 (Chart 2).

Chart 1a
Chemically synthesised sequence for IFNX416

ClaI

```
CGATAAGCTATGAGCTACAACTTGCTTGGATTCCTACAAAGAAGCAGCAATTTTCAGTCT
    TATTCGATACTCGATGTTGAACGAACCTAAGGATGTTTCTTCGTCGTTAAAAGTCAGA

CAGAAGCTCCTFTGGCAATTGAATGGGAGGCTTGAATATTGCCTCAAGGACAGGCACGAC
GTCTTCGAGGACACCGTTAACTTACCCTCCGAACTTATAACGGAGTTCCTGTCCGTGCTG

TTCGGCTTCCCTCAGGAAGAATTCGATGGCAATCAGTTTCAGAAAGAGGACGCCGCATTG
AAGCCGAAGGGAGTCCTTCTTAAGCTACCGTTAGTCAAAGTCTTTCTCCTGCGGCGTAAC

ACCATCTATGAGATGCTCCAGAACATCTTTGCTATTTTCAGACAAGATTCC
TGGTAGATACTCTACGAGGTCTTGTAGAAACGATAAAAGTCTGTTCTAAGGAGCT
```

XhoI

Chart 1b
Chemically synthesized sequence for IFNX417

ClaI

```
CGATAAGCTATGAGCTACAACTTGCTTGGATTCCTACAAAGAAGCAGCAATTTTCAGTCTC
    TATTCGATACTCGATGTTGAACGAACCTAAGGATGTTTCTTCGTCGTTAAAAGTCAGAG

AGAAGCTCCTGTGGCAATTGAATGGGAGGCTTGAATATTGCCTCAAGGACAGGCACGACTT
TCTTCGAGGACACCGTTAACTTACCCTCCGAACTTATAACGGAGTTCCTGTCCGTGCTGAA

CGGCTTCCCTGAGGAGATTAAGCAGCTGCAGCAGTTTCAGAAAGAGGACGCCGCATTGACC
GCCGAAGGGACTCCTCTAATTCGTCGACGTCGTCAAAGTCTTTCTCCTGCGGCGTAACTGG

ATCTATGAGATGCTCCAGAACATCTTTGCTATTTTCAGACAAGATTCC
TAGATACTCTACGAGGTCTTGTAGAAACGATAAAAGTCTGTTCTAAGGAGCT
```

XhoI

Chart 1c
Chemically synthesized sequence for IFNX418

ClaI

```
CGATAAGCTATGAGCTACAACTTGCTTGGATTCCTACAAAGAAGCAGCAATTTTCAGTCTCAG
    TATTCGATACTCGATGTTGAACGAACCTAAGGATGTTTCTTCGTCGTTAAAAGTCAGAGTC

AAGCTCCTGTGGCAATTGAATGGGAGGCTTGAATATTGCCTCAAGGACAGGATGAACTTTGAC
TTCGAGGACACCGTTAACTTACCCTCCGAACTTATAACGGAGTTCCTGTCCTACTTGAAACTG

ATCCCTCAGGAAGAATTCGATGGCAATCAGTTTCAGAAAGAGGACGCCGCATTGACCATCTAT
TAGGGAGTCCTTCTTAAGCTACCGTTAGTCAAAGTCTTTCTCCTGCGGCGTAACTGGTAGATA

GAGATGCTCCAGAACATCTTTGCTATTTTCAGACAAGATTCC
CTCTACGAGGTCTTGTAGAAACGATAAAAGTCTGTTCTAAGGAGCT
```

-continued
Chart 1c
Chemically synthesized sequence for IFNX418

XhoI

Chemical Synthesis of Gene Fragments

Oligodeoxyribonucleotides were synthesized by the phosphoramidite method (M. H. Caruthers, in "Chemical and Enzymatic synthesis of Gene Fragments", ed. H. G. Gasen and A. Lang, Verlag chemie, 1982, p.71) on controlled pore glass (H. Koster et al., Tetrahedron, 1984, 40, 103). Fully protected 2'-deoxyribonucleotide 3'-phosphoramidites were synthesized from the protected deoxyribonucleotide and chloro-N,N-(diisopropylamino)methoxyphosphine (L. J. McBride and M. H. Caruthers, Tetrahedron Lett., 1983, 24, 245 and S. A. Adams et al., J. Amer. Chem. Soc., 1983, 105, 661). Controlled pore glass supports were synthesized as described (F. Chow et al., Nuc. Acids Res., 1981, 9, 2807) giving 30–50 μmol deoxynucleoside per gram.

After completion of the synthesis, the protecting groups were removed and the oligomer cleaved from the support by sequential treatment with 3% (v/v) dichloroacetic acid/dichloromethane (120s), thiophenol/triethylamine/dioxan (1/1/2 v/v) (1 h) and concentrated ammonia at 70° C. (4 h). The deprotected oligonucleotides were purified either by HPLC on a Partisil® 10 SAX column using a gradient from 1M to 4M triethylammonium acetate pH4.9 at 50° C. or by electrophoresis on a denaturing 15% polyacrylamide gel (pH8.3).

Ligation of Oligonucleotide Blocks 500 pmole aliquots of the oligonucleotides were phosphorylated with 1 unit of T4 induced polynucleotide kinase in 20 μl of a solution containing 1000 pmole [$^{32}$p]γ-ATP (2.5 Ci/mMole), 100 μM spermidine, 20 mM DTT, 10 mM MgCl$_2$, 50 mM Tris-HCl (pH9.0) and 0.1 mM EDTA for 60 minutes at 37° C. The mixtures were then lyophilized and each oligonucleotide purified in a denaturing 15% polyacrylamide gel (pH8.3). After elution from the gel, the recovery was determined by counting the radioactivity.

Blocks (length 30–50 bases) were assembled by combining 25 pmole of each phosphorylated component with equimolar amounts of the unphosphorylated oligomers from the complementary strand. The mixtures were lyophilized and then taken up in 15 μl water and 2 μl 10×ligase buffer (500 mM Tris-HCl pH7.6, 100 mM MgCl$_2$). The blocks were annealed at 100° C. for 2 minutes, then slowly cooled to room temperature (20° C.). 2 μl 200 mM DTT and 0.5 μl 10 mM ATP were added to give final concentrations of 20 mM DTT and 250 μM ATP in 20 μl. 1.25 units of T4 DNA ligase were also added. After 18 hours at 20° C., the products were purified in a 15% polyacrylamide gel under denaturing conditions.

Two duplex blocks were then constructed from the single-stranded peices. (These were 150 base pairs and 75 base pairs). 1.5 pmole of each block were taken and the mixtures lyophilized. Annealing was carried out in 15 μl water and 2 μl 10×ligase buffer at 100° C. for 2 minutes, then slowly cooled to 10° C. 2 μl 200 mM DTT, 0.5 μl 10 mM ATP and 1.25 units T4 DNA ligase were added. The reaction was left at 10° C. for 18 hours. The products were then purified in a 10% native polyacrylamide gel.

The final product was assembled by combining 0.4 pmole of the two duplexes. The mixture was lyophilized and then taken up in 15 μl water and 2 μl 10×ligase buffer. It was annealed at 50° C. for 2 minutes and then slowly cooled to 10° C. 2 μl 20 mM DTT, 0.5 μl 10 mM ATP and 1.25 units ligase were then added and the reaction left at 10° C. for 18 hours. The final product was purified in a 5% native polyacrylamide gel. After elution and ethanol precipitation, the product was taken up in 10 μl water. 0.5 μl were removed for counting to calculate the recovery. 2 μl 10×ligase buffer, 2 μl 200 mM DTT, 2 μl 1 mM spermidine, 1 μl 10 mM ATP, 3 μl water and 0.5 units kinase were added to the rest (total volume 20 μl). The reaction was left at 37° C. for 1 hour and stopped by heating at 90° C. for 2 minutes. The final product was ethanol precipitated.

Construction of the plasmid pAP8 expressing IFNX416

Figure 2B:
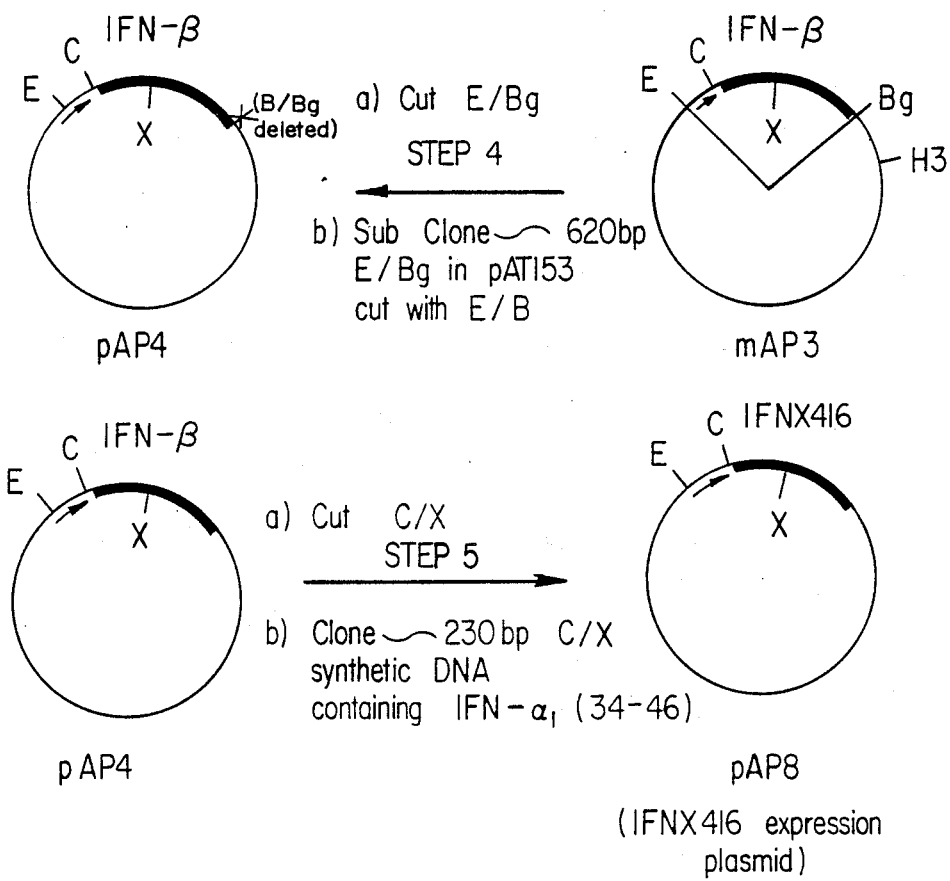

FIGS. 2(a) and 2(b) illustrate the path to constructing a high level expression vector for IFN-β[β(36–48-)→α$_1$(34–46)][cys$^{17}$]→[ser$^{17}$], also referred to as IFNX416, in the host E. coli HB101. The starting vector was p1/24C (~4,440 bp) which was identical to plasmid p1/24, except for the underlined sequences in Chart 3.

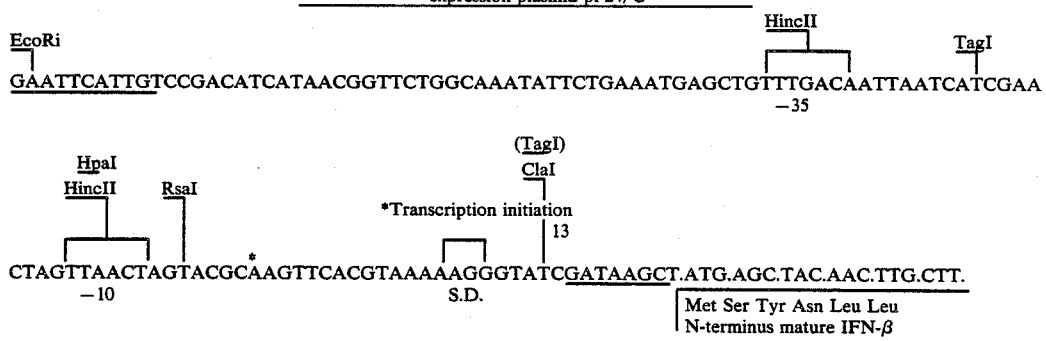

Chart 3
Nucleotide sequence of trp promoter region of IFN-β expression plasmid pl-24/C Step 1 (FIG. 2a)

The subcloning of the natural human IFN-β gene from plasmid p1/24C (Taniguchi et al., Gene, 10, 11, 1980) in phase M13 mp8 (Sanger, F. et al., J. Mol. Biol., 143, 161, 1981) was performed, and the presence of the whole fragment was confirmed by restriction endonuclease mapping of M13 plasmid mAP2.

Step 2 (FIG. 2a)

The technique of "site-directed mutagenesis" (Zoller and Smith, Nucl. Acids Res., 10, 6487, 1982) was employed to introduce two base changes, one each in the IFN-β codons 74 and 75 so as not to change the encoded amino acid sequence. Supercoiled DNA resulting from transcription/ligation was separated from non-ligated DNA in a 1% agarose gel and used to transform E. coli JM101. Total plasmid DNA was prepared.

Step 3 (FIG. 2a)

Mutant DNA bearing a unique XhoI site was separated from non-mutant DNA by XhoI restriction and electrophoresis in 1% agarose. The linear DNA was electroeluted from the agarose (Molecular cloning, A Laboratory Manual, eds. Maniatis et al., p. 168, Cold Spring Harbor Laboratories). Following self-ligation of the linear DNA and transformation of E. coli JM101, M13 clones were obtained all of which had a unique XhoI site, one of which was designated mAP3.

Step 4 (FIG. 2b)

The complete IFN-β gene with an XhoI site spanning codons 74–76 was recloned back in pAT153. This generated a vector (pAP4) similar to p1/24C, except for the changed codons 74 and 75 and the deletion of the ~546 base pair BglII-BamHI fragment, originally lying 3' to the IFN-β coding sequence. The new sequence of the Serine codons 74 and 75 is given in FIG. 2a.

Step 5 (FIG. 2b)

The ~230 bp synthetic DNA fragment, assembled as described above (displayed in FIG. 2a), was cloned in the ClaI-XhoI sites of plasmid pAP4 to give pAP8, a plasmid expressing IFNX416 in the host E. coli HB101. Clones with the correct structure were identified initially by the presence of additional TaqI and EcoRI restriction sites, and subsequently by complete nucleotide sequence analysis of the gene coding for IFNX416 (Maxam and Gilbert, Proc. Natl. Acad. Sci. U.S.A., 74, 560, 1977). The complete nucleotide sequence of the IFNX416 gene is shown in Chart 2. Plasmids pNW31 and pAP9 expressing IFNX417 and IFNX418, respectively, were prepared from plasmid pAP4 in an identical fashion, using ClaI-XhoI fragments of ~230 bp (Charts 1b and 1c), and the nucleotide sequences (Charts 2b and 2c) checked as above in the same way as for IFNX416. When the serine 17 was replaced by cysteine 17 the modified interferon was designated IFNX430 (Chart 2d).

Step 6 (Table 5)

Modified procedures for IFNX444; IFNX445, IFNX446, IFNX447, IFNX447, IFNX448, IFNX449, IFNX456, and IFNX485. Additional modified interferons were constructed by site-directed mutagenesis (Nucleic Acids Research 10, 6487 (1982) and 12, 9441 (1984)) with the oligonucleotide primers shown in Table 5. Following this site-directed mutagenesis of the DNA, a ClaI to XhoI fragment (~230 bp) of each IFNX shown in Table 5 was subcloned from the mutagenesis vector (FIG. 2a; plasmid in AP3 (betagene) or in AP4 (IFNX416 gene)) into the IFN beta expression vector (pAP4; FIG. 2b). Expression, biological evaluation and purification were carried out as described for IFNX416, X417, and X418.

TABLE 5

Summary of Construction of IFNX444-X485

1. Parent Sequences (human IFN-beta)
   5'-AAG.GAC.AGG.ATG.AAC.TTT.GAC.ATC.CCT.GAG.GAG.ATT.AAG.CAG.CTG.CAG.CAG.
   Lys Asp Arg Met Asn Phe Asp Ile Pro Glu Glu Ile Lys Gln Leu Gln Gln
   33      35      37      39      41      43      45      47      49

2. IFNX444 = IFN-beta (Gly-39)
   Oligonucleotide: CTACTTGAAACCCTAGGGACTCC-5'. The underlined nucleotides form a mismatch with codon 39.
   Gene mutagenized: IFN-beta
   New amino acid: Cly-39

3. IFNX445 = IFN-beta (Gly-47)
   Oligonucleotide: CTAATTCGTCCCTGTCGTCAAGG-5'. The underlined nucleotides form a mismatch with codon 47.
   Gene mutagenized: IFN-beta
   New amino acid: Gly-47

4. IFNX446 = IFN-beta (Gly-39; Gly-47)
   Oligonucleotide: CTAATTCGTCCCTGTCGTCAAGG-5'. The underlined nucleotides form a mismatch with codon 47.
   Gene mutagenized: IFNX444
   New amino acid: Gly-47

5. IFNX447 = IFNX416 (Arg-39; Ile-40)
   Oligonucleotide: CGTGCTGAAGGCCTAGGGAGTCCT-5'. The underlined nucleotides form a mismatch with codons 39 and 40.
   Gene mutagenized: IFNX416
   New amino acids. Arg-39; Ile-40.

6. IFNX448 = IFNX416 (Lys-36; Tyr-37)
   Oligonucleotide: TTCCTGTCCTTCATGAAGCCGAAG-5'. The underlined nucleotides form a mismatch with codons 36 and 37.
   Gene mutagenized: IFNX416
   New amino acids: Lys-36; Tyr-37

7. IFNX449 = IFNX416 (Gly-42)
   Oligonucleotide: CGAAGGGCCCACTTCTTAAGCTAC-5'. The underlined nucleotides form a mismatch with codon 42.
   Gene mutagenized: IFNX416.
   New amino acid: Gly-42.

8. IFNX456 = IFN-β(IFN-β[36–48]→IFN-α8[34–46])
   Starting plasmid pAP4 (FIG. 5b). Cut with ClaI-XhoI.

TABLE 5-continued
Summary of Construction of IFNX444-X485

Insert 230bp fragment of chemically synthesized DNA exactly as in construction of IFNX416 (FIG. 5b).

9. IFNX485 IFN-β(β[36–48]→mouseIFN-β[34–45]; Ser-17)
Starting plasmid pAP8 coding for IFNX416 (FIG. 5b)
Cut with ClaI and XhoI, replace with identical 236bp fragment
except that codon 20 (Leucine) of IFNX416 gene now -continued
Chart 2a
IFNX416

```
                    140                       145                         150
LYS—GLU—TYR—SER—HIS—CYS—ALA—TRP—THR—ILE—VAL—ARG—VAL—GLU—ILE—
AAR GAR TAY QZE CAY TGY GCN TGG ACN ATL GTN SGD GTN GAR ATL 165                       160                         165
LEU—ARG—ASN—PHE—TYR—PHE—ILE—ASN—ARG—LEU—THR—GLY—TYR—LEU—ARG—ASN—***—
YTB SGD AAY TTY TAY TTY ATL AAY SGD YTB ACN GGN TAY YTB SGD AAY TGA
```

SINGLE LETTER CODE FRAME 1

```
    10          20          30          40          50
MSYNLLGFLQ—RSSNFSQKL—LWQLNGRLEY—CLKDRHDFGF—PQEEFDGNQF—

60          70          80          90          100
QKEDAALTIY—EMLQNIFAIF—RQDSSSTGWN—ETIVENLLAN—VYHQINHLKT—

110         120         130         140         150
VLEEKLEKED—FTRGKLMSSL—HLKRYYGRIL—HYLKAKEYSH—CAWTIVRVEI—

160
LRNFYFINRL—TGYLRN<
```

Chart 2b
IFNX417

```
                5                          10                         15
MET—SER—TYR—ASN—LEU—LEU—GLY—PHE—LEU—GLN—ARG—SER—SER—ASN—PHE—
ATG QZE TAY AAY YTB YTB GGN TTY YTB CAR SGD QZE QZE AAY TTY 20                         25                         30
GLN—SER—GLN—LYS—LEU—LEU—TRP—GLN—LEU—ASN—GLY—ARG—LEU—GLU—TYR—
CAR QZE CAR AAR YTB YTB TGG CAR YTB AAY GGN SGD YTB GAR TAY 35                         40                         45
CYS—LEU—LYS—ASP—ARG—HIS—ASP—PHE—GLY—PHE—PRO—GLN—GLU—ILE—LYS—
TGY YTB AAR GAY SGD CAY GAY TTY GGN TTY CCN CAR GAR ATL AAR 50                         55                         60
GLN—LEU—GLN—GLN—PHE—GLN—LYS—GLU—ASP—ALA—ALA—LEU—THR—ILE—TYR—
CAR YTB CAR CAR TTY CAR AAR GAR GAY GCN GCN YTB ACN ATL TAY 65                         70                         75
GLU—MET—LEU—GLN—ASN—ILE—PHE—ALL—ILE—PHE—ARG—GLN—ASP—SER—SER—
GAR ATG YTB CAR AAY ATL TTY GCN ATL TTY SGD CAR GAY QZE QZE 80                         85                         90
SER—THR—GLY—TRP—ASN—GLU—THR—ILE—VAL—GLU—ASN—LEU—LEU—ALL—ASN—
QZE ACN GGN TGG AAY GAR ACN ATL GTN GAR

-continued
Chart 2b
IFNX417

160
LRNFYFINRL—TGYLRN<

Chart 2C
IFNX418

```
              5                       10                      15
MET—SER—TYR—ASN—LEU—LEU—GLY—PHE—LEU—GLN—ARG—SER—SER—ASN—PHE—
ATG QZE TAY AAY YTB YTB GGN TTY YTB CAR SGD QZE QZE AAY TTY 20                      25                      30
GLN—CYS—GLN—LYS—LEU—LEU—TRP—GLN—LEU—ASN—GLY—ARG—LEU—GLU—TYR—
CAR TGY CAR AAR YTB YTB TGG CAR YTB AAY GGN SGD YTB GAR TAY 35                      40                      45
CYS—LEU—LYS—ASP—ARG—MET—ASN—PHE—ASP—ILE—PRO—GLN—GLU—GLU—PHE—
TGY YTB AAR GAY SGD ATG AAY TTY GAY ATL CCN CAR GAR GAR TTY 50                      55                      60
ASP—GLY—ASN—GLN—PHE—GLN—LYS—GLU—ASP—ALA—ALA—LEU—THR—ILE—TYR—
GAY GGN AAY CAR TTY CAR AAR GAR GAY GCN GCN YTB ACN ATL TAY 65                      70                      75
GLU—MET—LEU—GLN—ASN—ILE—PHE—ALL—ILE—PHE—ARG—GLN—ASP—SER—SER—
GAR ATG YTB CAR AAY ATL TTY GCN ATL TTY SGD CAR GAY QZE QZE 80                      85                      90
SER—THR—GLY—TRP—ASN—GLU—THR—ILE—VAL—GLU—ASN—LEU—LEU—ALL—ASN—
QZE ACN GGN TGG AAY GAR ACN ATL GTN GAR AAY YTB YTB

Chart 2D
IFNX430

```
                35                              40                                45
CYS—LEU—LYS—ASP—ARG—HIS—ASP—PHE—GLY—PHE—PRO—GLN—GLU—GLU—PHE—
TGY YTB AAR GAY SGD CAY GAY TTY GGN TTY CCN CAR GAR GAR TTY 50                         55                         60
ASP—GLY—ASN—GLN—PHE—GLN—LYS—GLU—ASP—ALA—ALA—LEU—THR—ILE—TYR—
GAY GGN AAY CAR TTY CAR AAR GAR GAY GCN GCN YTB ACN ATL TAY 65                          70                          75
GLU—MET—LEU—GLN—ASN—ILE—PHE—ALL—ILE—PHE—ARG—GLN—ASP—SER—SER—
GAR ATG YTB CAR AAY ATL TTY GCN ATL TTY SGD CAR GAY QZE QZE 80                         85                         90
SER—THR—GLY—TRP—ASN—GLU—THR—ILE—VAL—GLU—ASN—LEU—LEU—ALL—ASN—
QZE ACN GGN TGG AAY GAR ACN ATL GTN GAR AAY YTB YTB GCN AAY 95                         100                        105
VAL—TYR—ILE—GLN—ILE—ASN—HIS—LEU—LYS—THR—VAL—LEU—GLU—GLU—LYS—
GTN TAY CAY CAR ATL AAY CAY YTB AAR ACN GTN

Chart 2e

```
                                110                                    115                              120
LEU—GLU—LYS—GLU—ASP—PHE—THR—ARG—GLY—LYS—LEU—MET—SER—SER—LEU—
YTB GAR AAR GAR GAY TTY ACN SGD GGN AAR YTB ATG QZE QZE YTB 125                              130                              135
HIS—LEU—LYS—ARG—TYR—TYR—GLY—ARG—ILE—LEU—HIS—TYR—LEU—LYS—ALA—
CAY YTB AAR SGD TAY TAY GGN SGD ATL YTB CAY TAY YTB AAR GCN 140                              145                              150
LYS—GLU—TYR—SER—HIS—CYS—ALA—TRP—THR—ILE—VAL—ARG—VAL—GLU—ILE—
AAR GAR TAY QZE CAY TGY GCN TGG ACN ATL GTN SGD GTN GAR ATL 155                              160                              165
LEU—ARG—ASN—PHE—TYR—PHE—ILE—ASN—ARG—LEU—THR—GLY—TYR—LEU—ARG—ASN-***-
YTB SGD AAY TTY TAY TTY ATL AAY SGD YTB ACN GGN TAY YTB SGD AAY TGA
```

SINGLE LETTER CODE FRAME 1

```
        10          20          30          40          50
MSYNLLGFLQ-RSSNFQCQKL-LWQLNGRLEY-CLKDRMNFGI-PEEIKQLQQF- 60          70          80          90          100
QKEDAALTIY-EMLQNIFAIF-RQDSSSTGWN-ETIVENLLAN-VYHQINHLKT- 110         120         130         140         150
VLEEKLEKED-FTRGKLMSSL-HLKRYYGRIL-HYLKAKEYSH-CAWTIVRVEI-

160
LRNFYFINRL-TGYLRN<
```

Chart 2f

IFNX445

```
                5                              10                              15
MET—SER—TYR—ASN—LEU—LEU—GLY—PHE—LEU—GLN—ARG—SER—SER—ASN—PHE—
ATG QZE TAY AAY YTB YTB GGN TTY YTB CAR SGD QZE QZE AAY TTY 20                              25                              30
GLN—CYS—GLN—LYS—LEU—LEU—TRP—GLN—LEU—ASN—GLY—ARG—LEU—GLU—TYR—
CAR TGY CAR AAR YTB YTB TGG CAR YTB AAY GGN SGD YTB GAR TAY 35                              40                              45
CYS—LEU—LYS—ASP—ARG—MET—ASN—PHE—ASP—ILE—PRO—GLU—GLU—ILE—LYS—
TGY YTB AAR GAY SGD ATG AAY TTY GAY ATL CCN GAR GAR ATL AAR 50                              55                              60
GLN—GLY—GLN—GLN—PHE—GLN—LYS—GLU—ASP—ALA—ALA—LEU—THR—ILE—TYR—
CAR GGN CAR CAR TTY CAR AAR GAR GAY GCN GCN YTB AC

-continued

Chart 2f

```
    110            120             130              140             150
VLEEKLEKED-FTRGKLMSSL-HLKRYYGRIL-HYLKAKEYSH-CAWTIVRVEI-

160
LRNFYFINRL-TGYLRN<
```

Chart 2g

IFNX446

```
                        5                        10                       15
MET—SER—TYR—ASN—LEU—LEU—GLY—PHE—LEU—GLN—ARG—SER—SER—ASN—PHE—
ATG QZE TAY AAY YTB YTB GGN TTY YTB CAR SGD QZE QZE AAY TTY 20                       25                       30
GLN—CYS—GLN—LYS—LEU—LEU—TRP—GLN—LEU—ASN—GLY—ARG—LEU—GLU—TYR—
CAR TGY CAR AAR YTB YTB TGG CAR YTB AAY GGN SGD YTB GA

Chart 2h -continued

```
                            50                      55                      60
ASP—GLY—ASN—GLN—PHE—GLN—LYS—GLU—ASP—ALA—ALA—LEU—THR—ILE—TYR—
GAY GGN AAY CAR TTY CAR AAR GAR GAY GCN GCN YTB ACN ATL TAY 65                      70                      75
GLU—MET—LEU—GLN—ASN—ILE—PHE—ALA—ILE—PHE—ARG—GLN—ASP—SER—SER—
GAR ATG YTB CAR AAY ATL TTY GCN ATL TTY SGD CAR GAY QZE QZE 80                      85                      90
SER—THR—GLY—TRP—ASN—GLU—THR—ILE—VAL—GLU—ASN—LEU—LEU—ALA—ASN—
QZE ACN GGN TGG AAY GAR ACN ATL GTN GAR AAY YTB YTB GCN AAY 95                      100                     105
VAL—TYR—HIS—GLN—ILE—ASN—HIS—LEU—LYS—THR—VAL—LEU—GLU—GLU—LYS—
GTN TAY CAY CAR ATL AAY CAY YTB AAR ACN GTN YTB GAR GAR AAR 110                     115                     120
LEU—GLU—LYS—GLU—ASP—PHE—THR—ARG—GLY—LYS—LEU—MET—SER—SER—LEU—
YTB GAR AAR GAR GAY TTY AC

-continued
Chart 2i
IFNX448

```
           130                      135
   —LEU—HIS—TYR—LEU—LYS—ALA—LYS—GLU—
    YTB CAY TAY YTB AAR GCN AAR GAR 140                      145
   —TYR—SER—HIS—CYS—ALA—TRP—THR—ILE—
    TAY QZE CAY TGY GCN TGG ACN ATL

150
   —VAL—ARG—VAL—GLU—ILE—LEU—ARG—ASN—
    GTN SGD GTN GAR ATL YTB SGD AAY 155                      160
   —PHE—TYR—PHE—ILE—ASN—ARG—LEU—THR—
    TTY TAY TTY ATL AAY SGD YTB ACN

165
                   —GLY—TYR—LEU—ARG—ASN—***—
                    GGN TAY YTB SGD AAY TGA
```

SINGLE LETTER CODE FRAME 1

```
   10         20         30
MSYNLLGFLQ—RSSNFQCQKL—LWQLNGRLEY—

40         50         60
—CLKDRKYFGF—PQEEFDGNQF—QKEDAALTIY—

70         80         90
—EMLQNIFAIF—RQDSSSTGWN—ETIVENLLAN—

100        110        120
—VYHQINHLKT—VLEEKLEKED—FTRGKLMSSL—

130        140        150
—HLKRYYGRIL—HYLKAKEYSH—CAWTIVRVEI—

160
         —LRNFYFINRL—TGYLRN<
```

Chart 2j
IFNX449

```
                   5
   MET—SER—TYR—ASN—LEU—LEU—GLY—PHE—LEU—
   ATG QZE TAY AAY YTB YTB GGN TTY YTB 10                  15
   —GLN—ARG—SER—SER—ASN—PHE—GLN—CYS—
    CAR SGD QZE QZE AAY TTY CAR TGY 20                  25
   —GLN—LYS—LEU—LEU—TRP—GLN—LEU—ASN—
    CAR AAR YTB YTB TGG CAR YTB AAY

30
   —GLY—ARG—LEU—GLU—TYR—CYS—LEU—LYS—
    GGN SGD YTB GAR TAY TGY YTB AAR 35                  40
   —ASP—ARG—HIS—ASP—PHE—GLY—PHE—PRO—
    GAY SGD CAY GAY TTY GGN TTY CON

45
   —GLY—GLU—GLU—PHE—ASP—GLY—ASN—GLN—
    GGN GAR GAR TTY GAY GGN AAY CAR 50                  55
   —PHE—GLN—LYS—GLU—ASP—ALA—ALA—LEU—
    TTY CAR AAR GAR GAY GCN GCN YTB 60              65
   —THR—ILE—TYR—GLU—MET—LEU—GLN—ASN—
    ACN ATL TAY GAR ATG YTB CAR AAY

70
   —ILE—PHE—ALA—ILE—PHE—ARG—GLN—ASP—
    ATL TTY GCN ATL TTY SGD CAR GAY
```

-continued
Chart 2j
IFNX449

```
            75                  80
   —SER—SER—SER—THR—GLY—TRP—ASN—GLU—
    QZE QZE QZE ACN GGN TGG AAY GAR

85
   —THR—ILE—VAL—GLU—ASN—LEU—LEU—ALA—
    ACN ATL GTN GAR AAY YTB YTB GCN 90                  95
   —ASN—VAL—TYR—HIS—GLN—ILE—ASN—HIS—
    AAY GTN TAY CAY CAR ATL AAY CAY 100             105
   —LEU—LYS—THR—VAL—LEU—GLU—GLU—LYS—
    YTB AAR ACN GTN YTB GAR GAR AAR

110
   —LEU—GLU—LYS—GLU—ASP—PHE—THR—ARG—
    YTB GAR AAR GAR GAY TTY ACN SGD 115                      120
   —GLY—LYS—LEU—MET—SER—SER—LEU—HIS—
    GGN AAR YTB ATG QZE QZE YTB CAY

125
   —LEU—LYS—ARG—TYR—TYR—GLY—ARG—ILE—
    YTB AAR SGD TAY TAY GGN SGD ATL 130                      135
   —LEU—HIS—TYR—LEU—LYS—ALA—LYS—GLU—
    YTB CAY TAY YTB AAR GCN AAR GAR 140                      145
   —TYR—SER—HIS—CYS—ALA—TRP—THR—ILE—
    TAY QZE CAY TGY GCN TGG ACN ATL

150
   —VAL—ARG—VAL—GLU—ILE—LEU—ARG—ASN—
    GTN SGD GTN GAR ATL YTB SGD AAY 155                      160
   —PHE—TYR—PHE—ILE—ASN—ARG—LEU—THR—
    TTY TAY TTY ATL AAY SGD YTB ACN

165
                   —GLY—TYR—LEU—ARG—ASN—***—
                    GGN TAY YTB SGD AAY TGA
```

SINGLE LETTER CODE FRAME 1

```
   10         20         30
MSYNLLGFLQ—RSSNFQCQKL—LWQLNGRLEY—

40         50         60
—CLKDRHDFGF—PGEEFDGNQF—QKEDAALTIY—

70         80         90
—EMLQNIFAIF—RQDSSSTGWN—ETIVENLLAN—

100        110        120
—VYHQINHLKT—VLEEKLEKED—FTRGKLMSSL—

130        140        150
—HLKRYYGRIL—HYLKAKEYSH—CAWTIVRVEI—

160
         —LRNFYFINRL—TGYLRN<
```

Chart 2k
IFNX456

```
                   5
   MET—SER—TYR—ASN—LEU—LEU—GLY—PHE—LEU—
   ATG QZE TAY AAY YTB YTB GGN TTY YTB
```

-continued
Chart 2k
IFNX456

10 15

—GLN—ARG—SER—SER—ASN—PHE—GLN—CYS—
CAR SGD QZE QZE AAY TTY CAR TGY 20 25

—GLN—LYS—LEU—LEU—TRP—GLN—LEU—ASN—
CAR AAR YTB YTB TGG CAR YTB AAY

30

—GLY—ARG—LEU—GLU—TYR—CYS—LEU—LYS—
GGN SGD YTB GAR TAY TGY YTB AAR 35 40

—ASP—ARG—HIS—ASP—PHE—GLU—PHE—PRO—
GAY SGD CAY GAY TTY GAR TTY CON

45

—GLN—GLU—GLU—PHE—ASP—ASP—LYS—GLN—
CAR GAR GAR TTY GAY GAY AAR CAR 50 55

—PHE—GLN—LYS—GLU—ASP—ALA—ALA—LEU—
TTY CAR AAR GAR GAY GCN GCN YTB 60 65

—THR—ILE—TYR—GLU—MET—LEU—GLN—ASN—
ACN ATL TAY GAR ATG YTB CAR AAY

70

—ILE—PHE—ALA—ILE—PHE—ARG—GLN—ASP—
ATL TTY GCN ATL TTY SGD CAR GAY 75 80

—SER—SER—SER—THR—GLY—TRP—ASN—GLU—
QZE QZE QZE ACN GGN TGG AAY GAR

85

—THR—ILE—VAL—GLU—ASN—LEU—LEU—ALA—
ACN ATL GTN GAR AAY YTB YTB GCN 90 95

—ASN—VAL—TYR—HIS—GLN—ILE—ASN—HIS—
AAY GTN TAY CAY CAR ATL AAY CAY 100 105

—LEU—LYS—THR—VAL—LEU—GLU—GLU—LYS—
YTB AAR ACN GTN YTB GAR GAR AAR

110

—LEU—GLU—LYS—GLU—ASP—PHE—THR—ARG—
YTB GAR AAR GAR GAY TTY ACN SGD 115 120

—GLY—LYS—LEU—MET—SER—SER—LEU—HIS—
GGN AAR YTB ATG QZE QZE YTB CAY

125

—LEU—LYS—ARG—TYR—TYR—GLY—ARG—ILE—
YTB AAR SGD TAY TAY GGN SGD ATL 130 135

—LEU—HIS—TYR—LEU—LYS—ALA—LYS—GLU—
YTB CAY TAY YTB AAR GCN AAR GAR 140 145

—TYR—SER—HIS—CYS—ALA—TRP—THR—ILE—
TAY QZE CAY TGY GCN TGG ACN ATL

150

—VAL—ARG—VAL—GLU—ILE—LEU—ARG—ASN—
GTN SGD GTN GAR ATL YTB SGD AAY 155 160

—PHE—TYR—PHE—ILE—ASN—ARG—LEU—THR—
TTY TAY TTY ATL AAY SGD YTB ACN

165

—GLY—TYR—LEU—ARG—ASN—***—
GGN TAY YTB SGD AAY TGA

-continued

Chart 2k

IFNX456

SINGLE LETTER CODE FRAME 1

10 20 30

MSYNLLGFLQ—RSSNFQCQKL—LWQLNGRLEY—

40 50 60

—CLKDRHDFEF—PQEEFDDKQF—QKEDAALTIY—

70 80 90

—EMLQNIFAIF—RQDSSSTGWN—ETIVENLLAN—

100 110 120

—VYHQINHLKT—VLEEKLEKED—FTRGKLMSSL—

130 140 150

—HLKRYYGRIL—HYLKAKEYSH—CAWTIVRVEI—

160

—LRNFYFINRL—TGYLRN<

Chart 2l

IFNX485

5

MET—SER—TYR—ASN—LEU—LEU—GLY—PHE—LEU—
ATG QZE TAY AAY YTB YTB GGN TTY YTB 10 15

—GLN—ARG—SER—SER—ASN—PHE—GLN—SER—
CAR SGD QZE QZE AAY TTY CAR QZE 20 25

—GLN—LYS—LEU—LEU—TRP—GLN—LEU—ASN—
CAR AAR YTB YTB TGG CAR YTB AAY

30

—GLY—ARG—LEU—GLU—TYR—CYS—LEU—LYS—
GGN SGD YTB GAR TAY TGY YTB AAR 35 40

—ASP—ARG—ALA—ASP—PHE—LYS—ILE—PRO—
GAY SGD GCN GAY TTY AAR ATL CON

45

—MET—GLU—MET—THR—GLU—LYS—GLN—PHE—
ATG GAR ATG ACN GAR AAR CAR TTY 50 55

—GLN—LYS—GLU—ASP—ALA—ALA—LEU—THR—
CAR AAR GAR GAY GCN GCN YTB ACN 60 65

—ILE—TYR—GLU—MET—LEU—GLN—ASN—ILE—
ATL TAY GAR ATG YTB CAR AAY ATL

70

—PHE—ALA—ILE—PHE—ARG—GLN—ASP—SER—
TTY GCN ATL TTY SGD CAR GAY QZE 75 80

—SER—SER—THR—GLY—TRP—ASN—GLU—THR—
QZE QZE ACN GGN TGG AAY GAR ACN

85

—ILE—VAL—GLU—ASN—LEU—LEU—ALA—ASN—
ATL GTN GAR AAY YTB YTB GCN AAY 90 95

—VAL—TYR—HIS—GLN—ILE—ASN—HIS—LEU—
GTN TAY CAY CAR ATL AAY CAY YTB 100 105

—LYS—THR—VAL—LEU—GLU—GLU—LYS—LEU—
AAR ACN GTN YTB GAR GAR AAR YTB

110

—GLU—LYS—GLU—ASP—PHE—THR—ARG—GLY—
GAR AAR GAR GAY TTY ACN SGD GGN

-continued
Chart 21
IFNX485

```
      115                                 120
—LYS—LEU—MET—SER—SER—LEU—HIS—LEU—
 AAR  YTB  ATG  QZE  QZE  YTB  CAY  YTB

125
—LYS—ARG—TYR—TYR—GLY—ARG—ILE—LEU—
 AAR  SGD  TAY  TAY  GGN  SGN  ATL  YTB 130                       135
—HIS—TYR—LEU—LYS—ALA—LYS—GLU—TYR—
 CAY  TAY  YTB  AAR  GCN  AAR  GAR  TAY 140                       145
—SER—HIS—CYS—ALA—TRP—THR—ILE—VAL—
 QZE  CAY  TGY  GCN  TGG  ACN  ATL  GTN

150
—ARG—VAL—GLU—ILE—LEU—ARG—ASN—PHE—
 SGD  GTN  GAR  ATL  YTB  SGD  AAY  TTY 155                           160
—TYR—PHE—ILE—ASN—ARG—LEU—THR—GLY—
 TAY  TTY  ATL  AAY  SGD  YTB  ACN  GGN

165
          —TYR—LEU—ARG—ASN—***—
           TAY  YTB  SGD  AAY  TGA
```

SINGLE LETTER CODE FRAME 1

```
10          20          30
MSYNLLGFLQ—RSSNFQSQKL—LWQLNGRLEY—

40          50          60
—CLKDRADFKI—PMEMTEKQFQ—KEDAALTIYE—

70          80          90
—MLQNIFAIFR—QDSSSTGWNE—TIVENLLANV—

100         110         120
—YHQINHLKTV—LEEKLEKEDF—TRGKLMSSLH—

130         140         150
—LKRYYGRILH—YLKAKEYSHC—AWTIVRVEIL—

160
                       —RNFYFINRLT—GYLRN<
```

EXAMPLE 2. ACTIVITY OF MODIFIED INTERFERONS

Expression of modified IFNs in *E. coli*

The plasmids pAP8, pNW31, pAP9, pJA20, pIL201 and pGC10 (FIG. 2*b*), were grown in the presence of a low level of tryptophan to an $OD_{600}$ of 0.5, then induced for IFN synthesis. pGC10 expresses IFN-$\beta$ to a high level and is identical to p1/24C (FIG. 2*a*) except that the ~546bp BG1II-BamHI fragment is deleted. pJA20 expresses IFN-$\beta$($Cys^{17}\rightarrow Ser^{17}$) also known as IFNX805 to a high level (the change of $Cys^{17}$ codon (TGT) to TCT(Serine) is described in U.K. Pat. No. 8,334,102). pJA20 is identical to plasmid p1/24 except for the loss of the ~546bp BglII-BamHI fragment, and a changed codon 17 (TGT→TCT:$Cys^{17}\rightarrow Ser^{17}$).

IFN-$\beta$($Cys^{17}\rightarrow Ser^{17}$)

(IFN805) and is included here for comparison.

The plasmid p1/24 is the parent plasmid of the plasmids in FIG. 2. Similiarly, plasmids pJA1, pJA2 and pJA3 can also be used to produce the modified interferons of this invention. The ATCC deposit number of *E. coli* HB101 containing pJA1 is 39520, pJA2 is 39521, and pJA3 is 39522. The ATCC is located at 12301 Parklawn Drive, Rockville, M.D. 20852, U.S.A.

The medium (25 ml) contained: M9 salts, 0.5% glucose, 0.1 mM $CaCl_2$, 0.5% casamino acids, 1 mM $MgSO_4$, 0.1 mg/ml vitamin $B_1$, 2.5 $\mu$g/ml tryptophan, and 100 $\mu$g/ml carbenecillin.

25 ml of warmed media was inoculated with 0.25 ml of an overnight culture of HB101/pAP8, HB101/pNW31, HB101/pAP9, HB101/pIL201, or HB101/pGC10 grown in the above medium (except for the presence of 42.5 $\mu$g/ml tryptophan) and grown at 37° C. with vigorous aeration. At $OD_{600}$ of 0.5, indole acrylic acid, the inducer of the *E. coli trp* promoter and therefore also of IFN synthesis, was added at 20 $\mu$g/ml. At 0.25 hr and 1.25 hr after induction, 1 mCi aliquots of $^{35}$S-labelled L-methionine 1000 Ci/mMole were introduced.

At 4–5 hours after induction 16 ml of culture was withdrawn ($OD_{600}$=0.75–1.2 range) and split as follows: (a) 14 ml was for estimation of "soluble" IFN antiviral activity; (b) 1 ml was for estimation of total "solubilized" IFN antiviral activity (the antiviral activity regained after a denaturation/renaturation cycle); and (c) 1 ml was for display of the total accumulated *E. coli* proteins plus IFN in a polyacrylamide gel (see below and FIG. 3).

Parallel cultures of 1 liter were also set up of HB101/pAP8, HB101/pAP9, HB101/pIL201, HB101/pJA20 and HB101/pGC10, in order to provide enough IFN-$\beta$ or modified IFN for purification (see "Purification of insoluble IFNs"—below). No radioactive label was added.

(a) Estimation of soluble IFN antiviral activity 14 ml of the 25 ml culture (see above) was centrifuged (6K rpm 5 min.) and the cell pellet washed twice in "lysozyme buffer"—30 mM tris-HCl pH7.5, 30 mM NaCl—then frozen. Pellets were vortexed in 1.4 ml lysozyme buffer, then incubated for 30 min. at 0° C. in the presence of 28 $\mu$l 10 mg/ml lysozyme and 3 $\mu$l 0.5M EDTA. The lysis was completed by three rapid freeze/-thaw cycles, and the lysate centrifuged at 17K rpm for 30 min. The supernatant was filtered through at 0.2 $\mu$M cellulose nitrate filter, and appropriate dilutions immediately assayed for IFN antiviral activity by monitoring the protection conferred on Vero cells against the cytopathic effect (cpe) of EMC virus in an in vitro microplate assay system (e.g. see Dahl and Degre, Acta. Path. Microbiol. Scan., 1380, 863, 1972). The diluent was 50 mM tris-HCl pH7.5, 30 mM NaCl, 1% human serum albumin (HSA).

(b) Estimation of TOTAL "solubized" IFN antiviral activity

For recovery of TOTAL "solubilized" IFN antiviral activity, the pellets from 1 ml of the 25 ml culture (see above) were vortexed in 20 $\mu$l "lysis buffer" per 0.1 $OD_{600}$ per ml of culture. ["Lysis buffer" is 5M urea, 30 mM NaCl, 50 mM Tris-HCl pH7.5, 1% SDS, 1% 2-mercaptoethanol, 1% HSA]. The mixture was heated for 2–3 min. at 90° C., frozen at −70° C. for 15 min., thawed and centrifuged at 17K rpm for 20 min. The supernatant was diluted in 1 log steps to 1:$10^5$, and IFN antiviral activity determined in Vero cells as above.

(c) Polyacrylamide gel electrophoresis of total polypeptides

Cells from 1 ml of 25 ml of of culture (see above) were mixed with 10 $\mu$l per 0.1 $OD_{600}$ per ml of final sample buffer: 5M urea, 1% SDS, 1% 2-mercaptoethanol, 50 mM Tris-HCl pH7.5, 30 mM NaCl and 0.05% bromophenol blue. The mixture was heated at 90° C. for 5 min., centrifuged for 10 min. and 5-7 µl loaded on a 15% acrylamide/0.4% bisacrylamide "Laemmli" gel. Electrophoresis was at 70 V for 18 hours. The gel was fixed and stained with Coomassie brilliant blue, then dried, photographed and autoradiographed (FIG. 3).

COMPARISON OF IFN PROTEIN EXPRESSION, ANTIVIRAL ACTIVITY AND ANTIPROLIFERATIVE ACTIVITY IN BACTERIAL EXTRACTS

Figure 3:
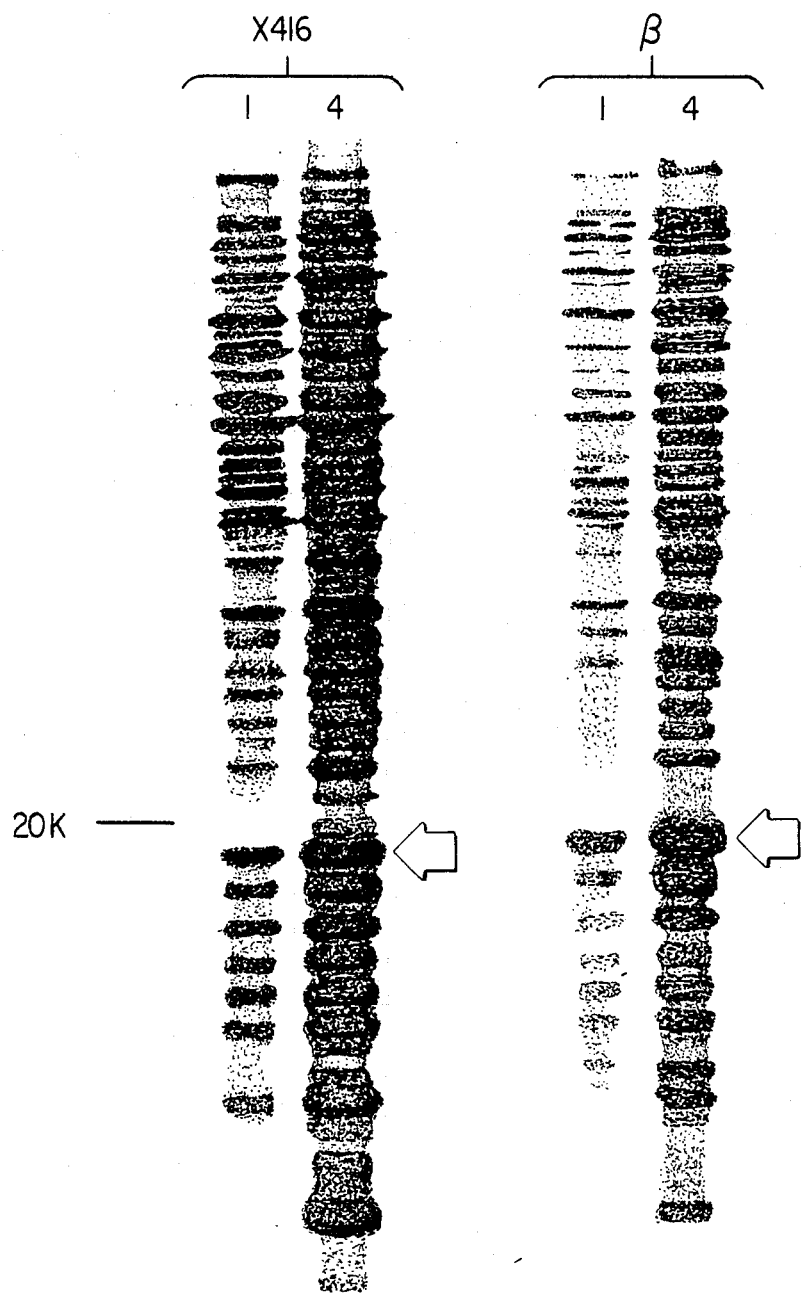

FIG. 3 and Table 1 demonstrate that the expression of IFNX416 is similar to that of IFN-$\beta$, yet the antiviral and antiproliferative activities of IFNX416 in bacterial extracts are approximately 200 times higher than that of IFN-$\beta$. The protein gel expression of IFNs X417 and X430 was similar to that of IFN X416 in FIG. 3. The antiviral and antiproliferative activities of IFN X417 and X430 in bacterial extracts were much higher than for IFN-$\beta$ (Table 1) and approached the values for IFN X416. These differences indicate a profound increase in antiviral and antiproliferative activity of IFN X416, X430 and X417 and/or improved renaturation, when compared with recombinant IFN-$\beta$. In contrast, IFN X418 had similar activities to IFN-$\beta$. These results also demonstrate that the improved biological activities of IFN X416 and X417 do not depend on the Cys$^{17}$ to Ser$^{17}$ alteration.

TABLE 1

Expression and Antiviral Activities of Novel, Modified Interferons in Bacterial Extracts

| IFNX No. | Expression (% total cell) | Antiviral Activity (IU/L/OD$_{600}$) | Antiproliferative activity (U/L/OD$_{600}$ at IC$_{50}$) |
|---|---|---|---|
| 416 | 5-15 | 0.36-2 × 10$^{10}$ | 1.3-1.4 × 10$^8$ |
| 417 | 5-15 | 0.4-4.4 × 10$^9$ | 0.54-1.0 × 10$^8$ |
| 418 | 10 | 5.4-6.5 × 10$^7$ | 2.2 × 10$^5$ |
| 430 | 5-15 | 1.1-5.0 × 10$^9$ | 2.1-6.0 × 10$^7$ |
| Beta | 5-15 | 0.5-2.0 × 10$^8$ | 4.6-6.8 × 10$^5$ |

U/L/OD$_{600}$ at IC$_{50}$ = dilution of bacterial extract giving 50% inhibition of cell growth.
IC$_{50}$ = Inhibitory concentration.
IU = International Units.

To confirm and extend these findings, IFN-$\beta$, IFNX416, IFNX418 and IFNX805 were subjected to purification, followed by simultaneous antiviral and antiproliferative assay, each on 3 different cell lines. Likewise, immunostimulating activity of IFNX416 was compared to IFN-$\beta$, IFNX418 and IFNX805 (see Tables 2, 3, 4). Later preparations of IFNX805 gave specific antiviral activities that varied in the range 10$^6$-10$^8$ units/mg.

TABLE 2

Antiviral Activity of Novel Modified Interferons (International Units/mg IFN Protein)

| IFNX No. | 17/1 | Chang | Vero |
|---|---|---|---|
| | CELL LINE | | |
| X430 | 3.3 × 10$^6$ | 3.1 × 10$^7$ | 2.7 × 10$^7$ |
| X416 | 3.8 × 10$^6$ | 3.2 × 10$^7$ | 2.0 × 10$^5$ |
| X418 | 7.1 × 10$^4$ | 7.8 × 10$^5$ | 2.4 × 10$^5$ |
| BETA | 1.3 × 10$^5$ | 5.1 × 10$^5$ | 7.6 × 10$^5$ |
| X805 | 7.6 × 10$^4$ | 4.4 × 10$^5$ | 4.2 × 10$^5$ |
| | RATIOS | | |
| X430/BETA | 25.0 | 62.0 | 35.5 |
| X416/BETA | 29.0 | 63.0 | 26.0 |
| X416/X805 | 50.0 | 73.0 | 48.0 |
| X418/BETA | 0.5 | 1.5 | 0.3 |

TABLE 2-continued

Antiviral Activity of Novel Modified Interferons (International Units/mg IFN Protein)

| IFNX No. | 17/1 | Chang | Vero |
|---|---|---|---|
| X805/BETA | 0.6 | 0.9 | 0.6 |

TABLE 3

Antiproliferative Activity of Novel Modified Interferons *(Units/mg IFN Protein)

| IFNX No. | HEP-2 | RD | DAUDI |
|---|---|---|---|
| | CELL LINE | | |
| X430 | 2.8 × 10$^5$ | 1.9 × 10$^5$ | 2.2 × 10$^6$ |
| X416 | 2.7 × 10$^5$ | 2.1 × 10$^5$ | 1.2 × 10$^6$ |
| X418 | 5.5 × 10$^3$ | 5.0 × 10$^3$ | 2.5 × 10$^3$ |
| BETA | 8.9 × 10$^3$ | 6.5 × 10$^3$ | 1.4 × 10$^4$ |
| X805 | 5.4 × 10$^3$ | 4.3 × 10$^3$ | 1.2 × 10$^4$ |
| | RATIOS | | |
| X430/BETA | 31.5 | 29.2 | 157.1 |
| X416/BETA | 30.0 | 32.0 | 86.0 |
| X416/X805 | 50.0 | 49.0 | 100.0 |
| X418/BETA | 0.6 | 0.8 | 0.2 |
| X805/BETA | 0.6 | 0.7 | 0.9 |

*Units = dilution at 50% inhibition of cell growth

TABLE 4

Immunomodulatory (ADCC) Activity of Novel Modified Interferons (Units/mg IFN Protein)

| IFNX No. | 1 | 2 | 3 | 4 | 5 |
|---|---|---|---|---|---|
| | DONOR | | | | |
| X416 | 7.1 × 10$^4$ | 1.1 × 10$^5$ | 3.9 × 10$^3$ | 9.5 × 10$^5$ | 3.0 × 10$^5$ |
| X418 | 3.5 × 10$^2$ | 1.7 × 10$^2$ | 1.8 × 10$^2$ | 3.0 × 10$^2$ | 1.2 × 10$^2$ |
| BETA | 1.0 × 10$^3$ | 1.9 × 10$^3$ | 1.1 × 10$^2$ | 1.1 × 10$^4$ | 1.7 × 10$^3$ |
| X805 | 4.5 × 10$^2$ | 3.2 × 10$^2$ | 1.5 × 10$^2$ | 1.8 × 10$^3$ | 5.8 × 10$^2$ |
| | RATIOS | | | | |
| X416/BETA | 71 | 58 | 35 | 86 | 176 |
| X416 | 158 | 344 | 26 | 528 | 517 |
| X418/BETA | 0.4 | 0.09 | 1.6 | 0.03 | 0.07 |
| X805/BETA | 0.5 | 0.2 | 1.4 | 0.2 | 0.3 |

PURIFICATION OF INSOLUBLE INTERFERONS

One liter of culture was induced and grown to OD$_{600}$ 1-2 as described above, except that no labelled amino acid was added. The cell pellet was resuspended in 30 ml 50 mM Tris-HCl pH8 and sonicated on ice, 4×1 min. at 100 W and then centrifuged for 1 hr at 15K rpm. 30 ml boiling extraction solution (50 mM Tris-HCl pH8, 50 mM DTT and 1-2% SDS) was added, mixed and the solution was sonicated. The solution was then boiled for 5 min., centrifuged for 1 hr at 15K rpm, and to the supernatant was added (NH$_4$)$_2$SO$_4$ to 40% saturation. After 15 min. the precipitate was collected by centrifugation at 10K rpm for 20 min. The pellet was redissolved by adding 5 ml warm 50 mM Tris-HCl pH8. Following a 15K rpm spin for 1 hour, the solution was re-reduced in 50 mM DTT by boiling for 5 min.

The IFNs were fractionated on a 2.35 cm×70 cm column of LKB AcA44 in 0.1% SDS, 50 mM Tris-HCl pH8, and the peak fractions containing 1-2 mg IFN were pooled.

To remove SDS and deplete pyrogens, either (a) the protein was acetone precipitated and redissolved in 50% formic acid, 10% isopropyl alcohol (solvent A); or (b) 6 parts formic acid and 1 part isopropyl alcohol were premixed and added to 3 parts sample. The mixture was applied to C-18 Sep-Pak ® (capacity greater than 3 mg) or to a C-18 Bond Elut (Anachem). The columns were first washed with Solvent A (2-4 ml) and the IFN eluted with 50% formic acid, 50% isopropyl alcohol.

The eluted IFN was dialysed against water to remove formate and then into Guanidium hydrochloride (6M), 100 mM Tris-HCl pH8. To renature the IFN, the sample was reduced in 10 mM DTT at 100° C., then diluted 100-fold into 100 mM Tris-HCl pH8, 200 mM KCl, 1 mM EDTA and either 0.1% Tween-20 or 1% HSA. Protein was estimated prior to biological assay.

ANTIVIRAL ASSAYS OF PURIFIED, MODIFIED INTERFERONS

A single virus (encephalomyocarditis—EMC) was used to determine antiviral activity in primate cells. Determinations were made with a virus cytopathic effect (cpe) assay following challenge of cells of Monkey (Vero) and human (Chang conjunctiva and Searle 17/1 fibroblast) origin (Dahl and Degre, ibid).

ANTIPROLIFERATIVE ASSAYS OF PURIFIED, NOVEL INTERFERONS

Antiproliferative activity was assessed by the ability of the IFN to inhibit the replication of three human cell lines (Horoszewicz et al., Science, 206, 1091, 1979)—Daudi (lymphoblastoid), HEP-2 (carcinoma) and RD (rhabdomyosarcoma). Daudi cells (in log phase) were cultured for 6 days in 96 well plates in the presence of various dilutions of interferon. The phenol red indicator in the medium changes from red to yellow (more acid) with progressive cell growth. Liquid paraffin was added to prevent pH change on exposure to the atmosphere and the pH change in the medium measured colorimetrically on a Dynatech plate reader. Interferon inhibition of cell growth is reflected by a corresponding reduction in the colour change. HEP-2 and RD in log growth were cultured for 3 days in 96 well plates in the presence of interferon. The cells were then fixed with 0.25% glutaraldehyde and stained with methylene blue. After extraction into ethanol the colour intensity was measured on a Dynatech plate reader. Once again colour intensity can be related proportionally to cell growth.

STIMULATION OF ANTIBODY-DEPENDENT CELLULAR CYTOTOXICITY BY NOVEL, MODIFIED INTERFERONS (ADCC)

ADCC represents a cellular system which is immunologically specific, the effect being mediated by antibody. There are several possible versions of this assay. $^{51}$Cr-labelled human red cells (GpA, Rh+ve) sensitized with anti-A antibody using the serum from a Group O individual were incubated with buffy coat cells from a Group O individual. Interferon was assessed by prior overnight incubation with buffy coat cells and its effects compared with those of parallel untreated controls (McCullagh et al., J. IFN Res., 3, 97, 1983).

THE IN VITRO ANTIVIRAL, ANTIPROLIFERATIVE AND IMMUNOSTIMULATING (ADCC) ACTIVITIES OF PURIFIED IFN-β, IFNX805, IFNX416 AND IFNX430

(a) Antiviral

Table 2 compares the antiviral activity of purified IFNs, including IFNX416 and X430, against EMC virus in three different cell lines. The antiviral activity of IFNX416 is in the range 26 to 63-fold higher than recombinant IFN-β, and 48 to 73-fold higher than IFNX805. Thus, IFNX416 displays a very significantly higher antiviral activity than IFN-β and IFNX805. This is in accord with the results described in Table 1, comparing IFNX416 and IFN-β present in crude bacterial extracts, for their antiviral activity in the EMC/Vero assay. Note that the antiviral activity of IFN-β is not significantly different from that of IFNX805. In contrast to IFNX416, the antiviral activity of IFNX418 is not significantly different from that of IFN-β.

(b) Antiproliferative

Table 3 compares the in vitro antiproliferative activity of purified IFNs, including IFNX416, in three different cell lines. The antiproliferative activity of IFNX416 is in the range 30 to 86-fold higher than IFN-β, and 49 to 100-fold higher than IFNX805. This is a highly significant increase in activity when compared to recombinant IFN-β or IFNX805. Again, in contrast to IFNX416, the antiproliferative activity of IFNX418 is similar to that of IFN-β and IFNX 805.

(c) Immunomodulatory (ADCC)

Table 4 compares the in vitro activity of purified IFNs, including IFNX416, as effectors of Antibody-Dependent Cellular Cytotoxicity (ADCC) against human red cells. IFNX416 is 35–176 times more potent than recombinant IFN-β, and 26–528 times more potent than IFNX805 in stimulating the cells of buffy coat preparations from five donors. This is a highly significant increase in activity when compared to recombinant IFN-β or IFNX805. IFNX418, on the other hand, was less effective than IFN-β as an effector of ADCC against the red cells from three of the five donors. The immunomodulatory activity (on ADCC) of IFNX416 and IFNX430 were compared. The IFNX416 specific activity was $1.85 \times 10^5$ units/mg and the IFNX430 specific activity was $2.77 \times 10^4$ units/mg protein.

PHARMACEUTICAL FORMULATION AND ADMINISTRATION

The novel, modified interferons of the present invention can be formulated by methods well known for pharmaceutical compositions, wherein the active interferon is combined in admixture with a pharmaceutically acceptable carrier substance, the nature of which depends on the particular mode of administration being used. Remington's Pharmaceutical Sciences by E. W. Martin, hereby incorporated by reference, describes compositions and formulations suitable for delivery of the inerferons of the present invention. For instance, parenteral formulations are usually injectable fluids that use physiologically acceptable fluids such as saline, balanced salt solutions, or the like as a vehicle. Oral formulations may be solid, e.g. tablet or capsule, or liquid solutions or suspensions.

The novel, modified interferons of the invention may be administered to humans or other animals on whose cells they are effective in various ways such as orally, intravenously, intramuscularly, intraperitoneally, intranasally, intradermally or subcutaneously. Administration of the interferon composition is indicated for patients with malignancies or neoplasms, whether or not immunosuppressed, or in patients requiring immunomodulation, or antiviral treatment. Dosage and dose rates may parallel those employed in conventional therapy with naturally occurring interferons—approximately $10^5$ to $10^8$ units daily. Dosages significantly above or below these levels may be indicated in long term administration or during acute short term treatment. A novel, modified inteferon may be combined with other treatments or used in association with other chemotherapeutic or chemopreventive agents for providing therapy against the above mentioned diseases and conditions, or other conditions against which it is effective.

Modifications of the above described mode for carrying out the invention such as, without limitation, use of alternative vectors, alternative expression control systems, and alternative host micro-organisms and other therapeutic or related uses of the novel interferons, that are obvious to those of ordinary skill in the biotechnology, pharmaceutical, medical and/or related fields are intended to be within the scope of the following claims.

We claim:

1. A gene comprising a recombinant DNA molecule encoding a polypeptide comprising a modified beta interferon comprising a beta interferon wherein amino acids 36 to 48 of said beta interferon are replaced by amino acids 34 to 46 of alpha 1 interferon and the cysteine at position 17 of said beta interferon is replaced by serine.

2. A gene comprising a recombinant DNA molecule encoding a polypeptide comprising a modified beta interferon comprising a beta interferon wherein amino acids 36 to 40 of said beta interferon are replaced by amino acids 34 to 38 of alpha 1 interferon and the cysteine at position 17 of said beta interferon is replaced by serine.

3. A gene comprising a recombinant DNA molecule encoding a polypeptide comprising a modified beta interferon comprising a beta interferon wherein amino acids 42 to 48 of said beta interferon are replaced by amino acids 40 to 46 of alpha 1 interferon.

4. A gene comprising a recombinant DNA molecule encoding a polypeptide comprising a modified beta interferon comprising a beta interferon wherein amino acids 36 to 48 of said beta interferon are replaced by amino acids 34 to 46 of alpha 1 interferon.

5. A recombinant plasmid comprising a replicating cloning vehicle in combination with the DNA sequence of claim 1.

6. A cell transformed by the recombinant plasmid of claim 5.

7. A recombinant plasmid comprising a replicating cloning vehicle in combination with the DNA sequence of claim 2.

8. A cell transformed by the recombinant plasmid of claim 7.

9. A recombinant plasmid comprising a replicating cloning vehicle in recombination with the DNA sequence of claim 3.

10. A cell transformed by the recombinant plasmid of claim 9.

11. A recombinant plasmid comprising a replicating cloning vehicle in combination with the DNA sequence of claim 4.

12. A cell transformed by the recombinant plasmid of claim 11.

* * * * *